United States Patent [19]

D'Sidocky

[11] 4,438,289

[45] Mar. 20, 1984

[54] REDUCTION OF CYCLOPENTADIENE FROM ISOPRENE STREAMS

[75] Inventor: Richard M. D'Sidocky, Ravenna, Ohio

[73] Assignee: The Goodyear Tire & Rubber Company, Akron, Ohio

[21] Appl. No.: 510,471

[22] Filed: Jul. 1, 1983

Related U.S. Application Data

[62] Division of Ser. No. 350,913, Feb. 22, 1982, Pat. No. 4,392,004.

[51] Int. Cl.$^3$ ............................ C07C 7/01; C07C 7/12
[52] U.S. Cl. ................................. 585/827; 585/820; 585/810; 585/829; 585/853; 208/310 R
[58] Field of Search ............... 585/809, 810, 820, 829, 585/853, 854, 827; 208/310 R

[56] References Cited

U.S. PATENT DOCUMENTS

| | | | |
|---|---|---|---|
| 2,935,540 | 5/1960 | Wolfe | 585/810 |
| 3,175,013 | 3/1965 | Smith | 585/839 |
| 3,209,050 | 9/1965 | Hanson | 585/829 |
| 3,285,989 | 11/1966 | Wolfe et al. | 585/837 |
| 3,538,179 | 11/1970 | Nelson | 585/853 |
| 3,686,349 | 8/1972 | Schliebs et al. | 585/803 |
| 3,692,861 | 9/1972 | Chikatsu et al. | 585/803 |
| 3,792,105 | 2/1974 | Siegmann | 585/854 |
| 3,864,422 | 2/1975 | Hein | 585/864 |
| 4,232,182 | 11/1980 | Liakumovich et al. | 585/820 |
| 4,392,004 | 7/1983 | D'Sidocky | 585/820 |

FOREIGN PATENT DOCUMENTS 47-15328  2/1968  Japan .................................. 585/820

*Primary Examiner*—Delbert E. Gantz
*Assistant Examiner*—A. Pal
*Attorney, Agent, or Firm*—D. O. Nickey

[57] ABSTRACT

A process for reducing the level of cyclopentadiene present in a hydrocarbon stream containing isoprene and cyclopentadiene which involves contacting the stream with a base wherein said base is selected from the group consisting of potassium hydroxide, sodium hydroxide and potassium fluoride. The base is situated on activated carbon carrier.

4 Claims, No Drawings

REDUCTION OF CYCLOPENTADIENE FROM ISOPRENE STREAMS

This is a divisional of application Ser. No. 350,913, filed Feb. 22, 1982, now U.S. Pat. No. 4,392,004.

BACKGROUND OF THE INVENTION

This application is directed to the reduction of very minute quantities of cyclopentadiene (hereinafter referred to as CPD) from hydrocarbon streams. It has been found that a number of hydrocarbon streams, particularly those containing mixtures of C-5 saturated hydrocarbons and unsaturated hydrocarbons containing, for instance, isoprene, pentane, pentene and CPD are of commercial value. However, CPD or dicyclopentadiene have an inhibiting effect on the subsequent polymerization of isoprene to cis-1, 4-polyisoprene. In the polymerization reaction, the Ziegler-Natta catalyst tends to be poisoned by the CPD.

To a large extent, many of the undesirable compounds can be removed by means of distillation of the hydrocarbon stream. However, because the boiling points of the C-5 hydrocarbon are very close, it is necessary to carry out distillation in columns having a large number of trays in order to achieve an adequate degree of separation. Such a distillation has been found to be technically and economically unattractive.

One known method for removal of CPD consists in binding CPD by carbonyl compounds such as benzaldehyde, salicylaldehyde, acetophenone, cyclopentanone in the presence of alkali metal alcoholates with the formation of the respective fulvenes. A decontaminated hydrocarbon is further treated with sodium bisulfate and water to remove said carbonyl compound and the fulvenes are distilled off. The disadvantage of this method is that the alkali metal alcoholate used therein as a catalyst is expensive and requires thorough dessication of the decontaminated hydrocarbon, the comsumption of the catalyst being important since it is decomposed by water released during the binding of CPD. Furthermore, the carbonyl compounds used are capable of being polymerized under the conditions of hydrocarbons decontamination resulting in clogging of equipment and excluding the possibility of stable operational conditions.

It is also possible to remove CPD from hydrocarbon mixtures by thermal dimerization and separation of the dimerized product from other hydrocarbons, such as isoprene, by means of distillation. However, dimerization takes a long time to decrease the amount of CPD to the very low concentrations permissible for isoprene polymerization, and still requires separation by distillation. Moreover, the resultant CPD dimers are of little commercial value.

Another known method for the removal of 1,3-CPD from an isoprene stream is by the addition of a solution of maleic anhydride in dimethyl formamide. The solution has a weight ratio of maleic anhydride to dimethyl foramide of about 2:1. This solution is added to the isoprene stream to give a 1.6 percent solution by weight which is allowed to react for 1½ hours without agitation. The CPD-maleic anhydride adduct and unreacted maleic anhydride are then removed from the isoprene stream by use of a caustic scrubber such as aqueous sodium hydroxide.

One known method for the removal of CPD from a hydrocarbon mixture containing isoprene consists of contacting the isoprene mixture with dehydrated molecular sieve material containing at least one alkali metal and having a pore diameter of more than 0.6 nanometers.

Another known method of decontaminating hydrocarbons used as solvents and monomers in the production of synthetic rubber by stereospecific polymerization from CPD which is present in the amount of 0.001–0.5 percent by weight of said hydrocarbons, comprises treating a mixture of said hydrocarbons and CPD with acyclic ketone having from 6 to 12 carbon atoms at a 10–2000 times stoichiometric-excess of said ketone with respect to CPD in the presence of a catalyst selected from the group consisting of alkali metal hydroxide or an anionic exchange resin in the (OH—) form thus obtaining a fulvene, said treatment taking place in the presence of 50 to 60 percent of a fulvene by weight of the hydrocarbons being decontaminated, said fulvene having been recycled together with unreacted ketone from a previous distillation of decontaminated hydrocarbons; and distilling off the decontaminated hydrocarbons containing not more than 0.0001 percent by weight of CPD. The disadvantage of this method is the required distillation of the hydrocarbon mixture.

Still another known process for purifying isoprene from mixtures thereof with carbonyl compounds and CPD produced by the catalytic decomposition of dimethyldioxane consists of the steps of passing the isoprene mixture at a temperature of from 40° to 70° C. through a bed of a solid product which comprises an anion exchange resin or an alkali, and subjecting said isoprene mixture to a fractionation with at least 50 theorectical plates and a reflux ratio of at least 3, recycling 20 to 80 weight percent of said purified isoprene following close fractionation for admixture with the starting isoprene to be purified.

SUMMARY OF THE INVENTION

Disclosed is a process for the removal of samll amounts of CPD from a C-5 hydrocarbon stream containing isoprene, pentane and CPD or dicyclopentadiene which comprises contacting said stream with activated carbon and a base representative of the group potassium hydroxide, sodium hydroxide and potassium fluoride.

DETAILED DESCRIPTION OF PREFERRED EMBODIMENTS

According to the present invention, there is provided a process for reducing amounts of CPD present in a hydrocarbon stream, particularly those containing mixtures of C-5 saturated hydrocarbons and unsaturated hydrocarbons, containing, for instance, isoprene, pentane and pentene comprising passing said stream through a bed of material wherein the bed material is selected from the group of activated carbon with potassium hydroxide, sodium hydroxide or potassium fluoride situated thereon.

One advantage of the present invention is that this process reduces the presence of CPD, in a hydrocarbon stream, to a tolerable level in the absence of subsequent distillation of said stream. This advantage will result in substantial savings in economy and time.

Activated carbon is an excellent adsorbent for the removal of small traces of impurities from a gas or liquid due to its high internal surface area and hence good adsorptive properties. It has been found that it is highly specific in action, adsorping one material and excluding others. One feature of adsorption by activated carbon is that the bulk of the adsorption can takes place at low relative pressures.

Adsorption is a term used to describe the existence of a higher concentration of a substance at the interface between a fluid and a solid than is present in the fluid. Adsorption can be by two types. The first type is physical adsorption. In physical adsorption, the impurities are held on the surface of the carbon by weak Van der Waals forces. The other method is chemisorption where the forces are relatively strong and occur at active sites on the surface, e.g. oxide groupings. It is known that the efficiency of the carbon will depend upon its accessible surface area and the presence of active sites upon the surface so that chemisorption may occur.

Activated carbons can be prepared in the laboratory from a large number of materials but those most commonly used in commercial practice are peat, lignite, coal, wood and coconut shell. The residues from carbonization and activation are found to have a large pore volume, and as this is derived from very small diameter pores, the internal surface area is high. Many commercial activated carbons have internal surfaces areas in the region of 1000 square meters per gram, and it is this enormous area which makes them effective adsorbents.

Commercially, activated carbon is produced by two methods. The first method is steam activation. Steam activated carbons are produced by a two-stage process. Initially, the material is carbonized and a coke is produced, the pores of which are either too small or constricted for it to be a useful adsorbent. The next stage is a process to enlarge the pore structure so that the internal surface is more accessible. This is achieved by reacting the semi-product with steam between 900° C. and 1000° C. At these temperatures the rate determining factor is the chemical reaction between the carbon and the steam. The reaction which takes place is at all the internal surfaces of the carbon, thus removing carbon from the pore walls and resulting in an enlarged pore diameter. As is known, the temperature of this reaction is very critical. At temperatures below 900° C. the rate of reaction is too slow to be economical. At temperatures in excess of 1100° C. the reaction becomes diffusion controlled and the reaction occurs in the outer layer of the carbon particles, thus reducing the particle in size without activating the interior. The second method of activation is chemical activation process. Chemically activated carbons are produced by mixing a chemical with a carbonatious material, usually wood, and carbonizing the resultant mixture. The carbonization temperature is usually in the range of 400° C. to about 500° C. The chemicals normally used for this activation process are phosphoric acid and zinc chloride solutions which swell the wood and open up the capillarity structure. Upon carbonization the chemical acts as a support and does not allow the char produced to shrink.

There are two types of classifications of activated carbon is relation to pH. The first type is the alkaline type. This is usually in the pH range of 7.5 or higher of the aqueous abstract. The second type is of the non-alkaline which is below a pH level of 7.5 of the aqueous abstract. The inorganic constituents of the basic raw material, which remain in the final activated carbon, contribute to the pH of the end product. During the production of the activated carbon, the temperature reached during manufacture is generally insufficiently high to volate these inorganic constituents. These constituents will be accessible to the product being purified and in many applications the presence of certain inorganic ions is undesirable. In the case of steam activated carbons, it is known that the best way to reduce the inorganic impurities is to acid wash the carbon, resulting in a non-alkaline activated carbon.

In practicing the present invention, the C-5 stream may be contacted with the activated carbon and base mounted thereon wherein the C-5 stream is in a vapor or liquid phase. The temperature may be selected within a wide range, preferably selected between 0° C. and 100° C. At temperatures above 100° C. there is a risk of polymerization of isoprene, whereas cooling of the hydrocarbon mixture to temperatures below 0° C. is often difficult.

It is believed that when the cyclopentadiene present in the C-5 stream comes in contact with the activated carbon and base situated thereon, an insoluble salt is formed in the bed of activated carbon and base. The fact remains that when the CPD in the hydrocarbon stream is collected in the base-activated carbon bed, there is an elimination of the requirement of subsequent distillation of the C-5 stream.

The LHSV of the volume of the feed stream is measured as the stream approaches the bed of activated carbon or activated carbon with an alkali compound mounted thereon. Liquid hour space velocity, hereinafter referred to as LHSV, is meant to mean a volume of liquid throughout per gross volume of catalyst which is the actual volume plus the interstitial volume. For example, 90 ml of liquid feed stock is passed over 45 cc (gross volume) of catalyst in one hour to yield an LHSV value of 2. See *Chemical Engineering Kinetics*, J. M. Smith, MacGraw-Hill, N.Y., pp. 99–100 (1956). As one skilled in the art would realize, if one has an excessive LHSV, the residence time of the feed stream with the base will be insufficient to convert the CPD to an insoluble salt. Accordingly, if the LHSV value is too low, it results in a residence time which would be commercially unfeasible. Preferably, the LHSV value is from 0.1 to 30.

The following examples are supplied in order to illustrate, but no necessarily to limit, the process of the present invention. All percentages are based upon weight unless stated otherwise.

EXAMPLES 1–3

50 ml of a C-5 hydrocarbon streams containing isoprene and CPD were contacted with activated charcoal. The activated carbon consisted of either the NonAlkaline or Alkaline Type. See Table I. The contact time for this example was 10 hours at 25° C. These runs were in a batch process, however, a continuous process can be conducted while staying within the scope of the present invention. The original CPD level was 12 part per million (by weight based upon overall weight of stream) of the stream.

TABLE I

| | CPD Removal Using Activated Charcoal | | | |
|---|---|---|---|---|
| Ex. | Carbon | Carbon Amount | Original % Isoprene | After Treatment Isoprene | % CPD Removed |
| 1 | Non Alkaline | 1 g | 5.3 | 5.2 | 66 |
| 2 | Non Alkaline | 5 g | 5.3 | 5.0 | 100 |
| 3 | Alkaline | 1 g | 5.3 | 5.2 | 100 |

EXAMPLES 4-12

50 ml of a C-5 hydrocarbon streams containing isoprene and CPD were contacted with various bases on an activated carbon carrier. The contact time for this example was 10 hr. at 25° C. These runs were in a batch process, however, a continuous process can be conducted while staying within the scope of the present invention. The original CPD level was 12 ppm. The percentage of base is the ratio of weight of base to overall weight of support and base.

TABLE II

| Ex. | Carbon Support | Base | Original % Isoprene | After Treatment % Isoprene | % CPD Removed |
|---|---|---|---|---|---|
| 4 | 1 g Non Alk | 5% KF | 5.3 | 5.3 | 75% |
| 5 | 5 g Non Alk | 5% KF | 5.3 | 5.2 | 100% |
| 6 | 1 g Non Alk | 10% KF | 5.3 | 5.4 | 100% |
| 7 | 1 g Non Alk | 20% KF | 5.3 | 5.2 | 100% |
| 8 | 1 g Non Alk | 40% KF | 5.3 | 5.2 | 100% |
| 9 | 1 g Non Alk | 5% NaOH | 5.3 | 5.2 | 100% |
| 10 | 1 g Non Alk | 10% NaOH | 5.3 | 5.1 | 100% |
| 11 | 1 g Non Alk | 20% NaOH | 5.3 | 5.1 | 100% |
| 12 | 1 g Non Alk | 40% NaOH | 5.3 | 5.5 | 100% |

EXAMPLE 13

A continuous run was made using a fixed-bed of Alkaline carbon while metering the C-5 hydrocarbon stream containing 5.4% isoprene and 14 ppm of CPD. The stream was directed in an up-flow manner through the bed at an LHSV of 1.62 for 4.88 hours. After this time, no CPD was detectable in the collected feed. The percentage of isoprene collected was 5.3% of the stream.

EXAMPLES 14 AND 15

50 ml of C-5 hydrocarbon streams containing isoprene and 21 ppm of CPD were contacted with the following (See Table III) for a period of two hours at 25° C. The percentage of base is the ratio of the weight of base to overall weight of loaded support.

TABLE III

| Ex. | Carbon | Base | Original % Isoprene | After Treatment % Isoprene | % CPD Removed |
|---|---|---|---|---|---|
| 14 | 1 g Alkaline | None | 5.4 | 5.5 | 47% |
| 15 | 1 g Alkaline | 20% KF | 5.4 | 5.6 | 95% |

EXAMPLES 16-71

100 grams of C-5 hydrocarbon streams containing 5% by wgt. isoprene and 14 ppm of CPD were contacted with the following (See Table IV). The contact time for this example was 1 hour and the temperatures were held at 35° C. The percentage of base is the ratio of the weight of base to overall weight of loaded support.

TABLE IV

| Ex. | C-5 Solution | Contact Time-Hrs | Base | | Support | % Isoprene | Original CPD PPM | After CPD PPM | % CPD Removal |
|---|---|---|---|---|---|---|---|---|---|
| 16 | 100 gms | 1 | 10% KOH | 1 gm | Activated Alk. Carbon | 5.0 | 14 | 4 | 71 |
| 17 | 100 gms | 1 | 10% KOH | 2 gms | Activated Alk. Carbon | 5.0 | 14 | 1 | 93 |
| 18 | 100 gms | 1 | 10% KOH | 4 gms | Activated Alk. Carbon | 5.0 | 14 | 0 | 100 |
| 19 | 100 gms | 1 | 10% KOH | 5 gms | Activated Alk. Carbon | 5.0 | 14 | 0 | 100 |
| 20 | 100 gms | 1 | 5% KOH | 1 gm | Activated Alk. Carbon | 5.0 | 14 | 9 | 36 |
| 21 | 100 gms | 1 | 5% KOH | 2 gms | Activated Alk. Carbon | 5.0 | 14 | 4 | 71 |
| 22 | 100 gms | 1 | 5% KOH | 4 gms | Activated Alk. Carbon | 5.0 | 14 | 0 | 100 |
| 23 | 100 gms | 1 | 5% KOH | 5 gms | Activated Alk. Carbon | 5.0 | 14 | 0 | 100 |
| 24 | 100 gms | 1 | 5% NaOH | 1 gm | Activated Alk. Carbon | 5.0 | 14 | 12 | 15 |
| 25 | 100 gms | 1 | 5% NaOH | 2 gms | Activated Alk. Carbon | 5.0 | 14 | 4 | 71 |
| 26 | 100 gms | 1 | 5% NaOH | 4 gms | Activated Alk. Carbon | 5.0 | 14 | 1 | 93 |
| 27 | 100 gms | 1 | 5% NaOH | 5 gms | Activated Alk. Carbon | 5.0 | 14 | 0 | 100 |
| 28 | 100 gms | 1 | 5% KOH | 0 gm | Activated Alk. Carbon | 5.7 | 14-15 | 13 | 7-13 |
| 29 | 100 gms | 1 | 5% KOH | 1 gm | Activated Alk. Carbon | 5.6 | 14-15 | 9 | 36-40 |
| 30 | 100 gms | 1 | 5% KOH | 2 gms | Activated Alk. Carbon | 5.6 | 14-15 | 4 | 72-74 |
| 31 | 100 gms | 1 | 5% KOH | 4 gms | Activated Alk. Carbon | 5.6 | 14-15 | 0 | 100 |
| 32 | 100 gms | 1 | 5% KOH | 5 gms | Activated Alk. Carbon | 5.6 | 14-15 | 0 | 100 |
| 33 | 100 gms | 1 | 10% KOH | 0 gm | Activated Alk. Carbon | 5.8 | 14-15 | 13 | 7-13 |
| 34 | 100 gms | 1 | 10% KOH | 1 gm | Activated Alk. Carbon | 5.8 | 14-15 | 4 | 72-74 |
| 35 | 100 gms | 1 | 10% KOH | 2 gms | Activated Alk. Carbon | 5.8 | 14-15 | 1 | 93-94 |
| 36 | 100 gms | 1 | 10% KOH | 4 gms | Activated Alk. Carbon | 5.8 | 14-15 | 0 | 100 |
| 37 | 100 gms | 1 | 10% KOH | 5 gms | Activated Alk. Carbon | 5.6 | 14-15 | 0 | 100 |

TABLE IV-continued

| Ex. | C-5 Solution | Contact Time-Hrs | Base | | Support | % Isoprene | Original CPD PPM | After CPD PPM | % CPD Removal |
|---|---|---|---|---|---|---|---|---|---|
| 38 | 100 gms | 1 | 20% KOH | 0 gm | Activated Alk. Carbon | 5.4 | 14–15 | 15 | 0 |
| 39 | 100 gms | 1 | 20% KOH | 1 gm | Activated Alk. Carbon | 5.4 | 14–15 | 11 | 21–27 |
| 40 | 100 gms | 1 | 20% KOH | 2 gms | Activated Alk. Carbon | 5.4 | 14–15 | 9 | 36–40 |
| 41 | 100 gms | 1 | 20% KOH | 4 gms | Activated Alk. Carbon | 5.4 | 14–15 | 3 | 79–80 |
| 42 | 100 gms | 1 | 20% KOH | 5 gms | Activated Alk. Carbon | 5.4 | 14–15 | 1 | 93–94 |
| 43 | 100 gms | 1 | 5% NaOH | 0 gm | Activated Alk. Carbon | 5.6 | 14–15 | 14 | 0–6 |
| 44 | 100 gms | 1 | 5% NaOH | 1 gm | Activated Alk. Carbon | 5.7 | 14–15 | 12 | 15–20 |
| 45 | 100 gms | 1 | 5% NaOH | 2 gms | Activated Alk. Carbon | 5.6 | 14–15 | 4 | 72–74 |
| 46 | 100 gms | 1 | 5% NaOH | 4 gms | Activated Alk. Carbon | 5.6 | 14–15 | 1 | 93–94 |
| 47 | 100 gms | 1 | 5% NaOH | 5 gms | Activated Alk. Carbon | 5.6 | 14–15 | 0 | 100 |
| 48 | 100 gms | 1 | 10% NaOH | 0 gm | Activated Alk. Carbon | 5.5 | 14–15 | 15 | 0 |
| 49 | 100 gms | 1 | 10% NaOH | 1 gm | Activated Alk. Carbon | 5.5 | 14–15 | 12 | 15–20 |
| 50 | 100 gms | 1 | 10% NaOH | 2 gms | Activated Alk. Carbon | 5.5 | 14–15 | 8 | 43–47 |
| 51 | 100 gms | 1 | 10% NaOH | 4 gms | Activated Alk. Carbon | 5.5 | 14–15 | 4 | 72–74 |
| 52 | 100 gms | 1 | 10% NaOH | 5 gms | Activated Alk. Carbon | 5.5 | 14–15 | 2 | 86–87 |
| 53 | 100 gms | 1 | 20% NaOH | 0 gm | Activated Alk. Carbon | 5.6 | 14–15 | 14 | 0–6 |
| 54 | 100 gms | 1 | 20% NaOH | 1 gm | Activated Alk. Carbon | 5.6 | 14–15 | 13 | 7–13 |
| 55 | 100 gms | 1 | 20% NaOH | 2 gms | Activated Alk. Carbon | 5.6 | 14–15 | 11 | 21–27 |
| 56 | 100 gms | 1 | 20% NaOH | 4 gms | Activated Alk. Carbon | 5.6 | 14–15 | 7 | 50–54 |
| 57 | 100 gms | 1 | 20% NaOH | 5 gms | Activated Alk. Carbon | 5.6 | 14–15 | 5 | 65–66 |
| 58 | 100 gms | 1 | — | 0 gm | Activated Alk. Carbon-untreated (Undried) Wet | 5.4 | 14–15 | 15 | 0 |
| 59 | 100 gms | 1 | — | 1 gm | Activated Alk. Carbon-untreated (Undried) Wet | 5.4 | 14–15 | 11 | 21–27 |
| 60 | 100 gms | 1 | — | 2 gms | Activated Alk. Carbon-untreated (Undried) Wet | 5.4 | 14–15 | 9 | 36–40 |
| 61 | 100 gms | 1 | — | 4 gms | Activated Alk. Carbon-untreated (Undried) Wet | 5.4 | 14–15 | 3 | 79–80 |
| 62 | 100 gms | 1 | — | 5 gms | Activated Alk. Carbon-untreated (Undried) Wet | 5.4 | 14–15 | 1 | 93–94 |
| 63 | 100 gms | 1 | — | 0 gm | Activated Alk. Carbon AZO (dried & ground) | 5.6 | 14–15 | 14 | 0–6 |
| 64 | 100 gms | 1 | — | 1 gm | Activated Alk. Carbon AZO (dried & ground) | 5.6 | 14–15 | 12 | 15–20 |
| 65 | 100 gms | 1 | — | 2 gms | Activated Alk. Carbon AZO (dried & ground) | 5.6 | 14–15 | 10 | 29–33 |
| 66 | 100 gms | 1 | — | 4 gms | Activated Alk. Carbon AZO (dried & ground) | 5.6 | 14–15 | 6 | 57–60 |
| 67 | 100 gms | 1 | — | 5 gms | Activated Alk. Carbon AZO (dried & ground) | 5.6 | 14–15 | 4 | 72–74 |
| 68 | 100 gms | 1 | — | 0 gm | Activated Alk. Carbon 35 × 100 (dried & ground) | 5.6 | 14–15 | 15 | 0 |
| 69 | 100 gms | 1 | — | 1 gm | Activated Alk. Carbon 35 × 100 (dried & ground) | 5.5 | 14–15 | 15 | 0 |
| 70 | 100 gms | 1 | — | 2 gms | Activated Alk. Carbon 35 × 100 (dried & ground) | 5.5 | 14–15 | 15 | 0 |

TABLE IV-continued

| Ex. | C-5 Solution | Contact Time-Hrs | Base | Support | % Isoprene | Original CPD PPM | After CPD PPM | % CPD Removal |
|---|---|---|---|---|---|---|---|---|
| 71 | 100 gms | 1 | — | 4 gms Activated Alk. Carbon 35 × 100 (dried & ground) | 5.5 | 14–15 | 6 | 57–60 |

EXAMPLES 72–79

For the purposes of comparison, the following examples were run. Base compounds on various inert carriers were contacted with 50 ml of a C-5 hydrocarbon stream containing isoprene and 21 ppm of CPD. The contact time was 2 hours and the temperature of the stream was 25° C. The loaded support weighed 1 gram.

TABLE V

| Ex. | Support | Base | Original Isoprene | After Treatment % Isoprene | % CPD Removal |
|---|---|---|---|---|---|
| 72 | Celite | 20% KF | 5.4 | 5.6 | 5% |
| 73 | Celite | None | 5.4 | 5.6 | 5% |
| 74 | Al$_2$O$_3$ | 20% KF | 5.4 | 5.6 | 14% |
| 75 | Al$_2$O$_3$ | 20% NaOH | 5.4 | 5.6 | 0% |
| 76 | Al$_2$O$_3$ | None | 5.4 | 5.6 | 0% |
| 77 | SiO$_2$ | None | 5.4 | 5.4 | 38% |
| 78 | SiO$_2$ | 20% KF | 5.4 | 5.5 | 0% |

TABLE V-continued

| Ex. | Support | Base | Original Isoprene | After Treatment % Isoprene | % CPD Removal |
|---|---|---|---|---|---|
| 79 | SiO$_2$ | 20% NaOH | 5.4 | 5.5 | 5% |

While certain representative embodiments and details have been shown for the purpose of illustrating the invention, it will be apparent to those skilled in the art that various changes and modifications may be made therein without departing from the scope of the invention.

I claim:

1. A process for the removal of small amounts of cyclopentadiene (CPD) from a C-5 hydrocarbon stream which comprises contacting said stream with activated carbon.

2. A process as claimed in claim 1 wherein said stream is at a temperature of from 0° C. to 100° C.

3. A process as claimed in claim 2 wherein said stream has an LHSV value of from 0.5 to 30.

4. A process as claimed in claim 2 wherein said temperature is from 15° C. to 60° C.

* * * * *

UNITED STATES PATENT AND TRADEMARK OFFICE
CERTIFICATE OF CORRECTION

PATENT NO. : 4,438,289
DATED : Mar. 20, 1984
INVENTOR(S) : Richard M. D'Sidocky

It is certified that error appears in the above-identified patent and that said Letters Patent is hereby corrected as shown below:

Column 2, line 39, delete "saml1" and insert therefor --small--.

Column 3, line 59, delete "is" after the word carbon and insert therefor --in--.

Column 4, line 32, delete the three dots before cc and insert therefor --45--.

Signed and Sealed this

Thirtieth Day of October 1984

[SEAL]

Attest:

GERALD J. MOSSINGHOFF

Attesting Officer

Commissioner of Patents and Trademarks